US012274661B2

(12) United States Patent
Jeong

(10) Patent No.: US 12,274,661 B2
(45) Date of Patent: Apr. 15, 2025

(54) FACIAL MASK FOR SKIN CARE

(71) Applicant: AMOSENSE CO., LTD, Cheonan-si (KR)

(72) Inventor: Sang Dong Jeong, Gimpo-si (KR)

(73) Assignee: AMOSENSE CO., LTD., Cheonan-si (KR)

( * ) Notice: Subject to any disclaimer, the term of this patent is extended or adjusted under 35 U.S.C. 154(b) by 640 days.

(21) Appl. No.: 17/613,201

(22) PCT Filed: Jun. 12, 2020

(86) PCT No.: PCT/KR2020/007671
§ 371 (c)(1),
(2) Date: Nov. 22, 2021

(87) PCT Pub. No.: WO2020/251310
PCT Pub. Date: Dec. 17, 2020

(65) Prior Publication Data
US 2022/0241146 A1   Aug. 4, 2022

(30) Foreign Application Priority Data
Jun. 14, 2019   (KR) .................. 10-2019-0070372

(51) Int. Cl.
*A61H 23/02* (2006.01)
*A41D 13/11* (2006.01)
(Continued)

(52) U.S. Cl.
CPC .............. *A61H 23/02* (2013.01); *A41D 13/11* (2013.01); *A45D 44/002* (2013.01);
(Continued)

(58) Field of Classification Search
CPC .... A61H 23/00; A61H 23/02; A61H 23/0218; A61H 23/0236; A61H 2205/022;
(Continued)

(56) References Cited

U.S. PATENT DOCUMENTS

| 4,841,954 A | * | 6/1989 | Kalsi ................. A61H 23/0263 601/71 |
| 2003/0056281 A1 | * | 3/2003 | Hasegawa .............. A61N 2/002 2/206 |
| 2009/0069727 A1 | * | 3/2009 | Neustaedter ....... A61H 23/0263 600/587 |
| 2011/0172573 A1 | | 7/2011 | Wallace |

(Continued)

FOREIGN PATENT DOCUMENTS

| JP | 2005118527 A | 5/2005 |
| KR | 10-2011-0048641 A | 5/2011 |

(Continued)

OTHER PUBLICATIONS

International Search Report Issued in PCT/KR2020/007671 dated Sep. 21, 2020, 4 pages.

*Primary Examiner* — Rachel T Sippel
*Assistant Examiner* — Gwynneth L Howell
(74) *Attorney, Agent, or Firm* — ROTHWELL, FIGG, ERNST & MANBECK, P.C.

(57) ABSTRACT

Provided is a skin care mask. The skin care mask includes a mask member configured to be placed on a facial region of a human body. The skin care mask further includes one or more vibrators installed within the mask member and configured to transfer vibrations to skin of the human body. The skin care mask further includes a vibration transfer member including a first surface contacting the one or more vibrators and a second surface configured to contact the skin. The vibration transfer member is configured to transfer the vibrations of the one or more vibrators to the skin. The skin care mask further includes a vibration absorption member. The skin care mask further includes a processor configured to separately control the one or more vibrators.

16 Claims, 2 Drawing Sheets

(51) Int. Cl.
*A45D 44/00* (2006.01)
*A61N 5/06* (2006.01)

(52) U.S. Cl.
CPC ...... *A61N 5/0616* (2013.01); *A45D 2200/155* (2013.01); *A45D 2200/205* (2013.01); *A45D 2200/207* (2013.01); *A61H 2201/0165* (2013.01); *A61H 2201/0207* (2013.01); *A61H 2201/10* (2013.01); *A61H 2201/165* (2013.01); *A61H 2201/5002* (2013.01); *A61H 2205/022* (2013.01); *A61N 2005/0647* (2013.01); *A61N 2005/0652* (2013.01)

(58) Field of Classification Search
CPC .... A61H 2023/0209; A61H 2023/0227; A61H 39/04; A61H 2201/165; A61H 2201/1604; A61H 2201/0165; A61H 9/00; A61H 15/00; A61H 7/00; A45D 44/002; A45D 44/22; A45D 2200/207; A41D 13/11
See application file for complete search history.

(56) References Cited

U.S. PATENT DOCUMENTS

| | | | |
|---|---|---|---|
| 2012/0022411 A1* | 1/2012 | Wu | A61N 1/046 601/15 |
| 2014/0142477 A1 | 5/2014 | Park | |
| 2014/0163438 A1* | 6/2014 | Park | A61H 23/02 601/46 |
| 2017/0181923 A1* | 6/2017 | Thorpe | A61H 9/0078 |
| 2017/0181924 A1* | 6/2017 | Thorpe | A61H 7/002 |
| 2021/0369557 A1* | 12/2021 | Shin | A61H 23/0254 |
| 2022/0211162 A1* | 7/2022 | Kim | A61K 8/02 |

FOREIGN PATENT DOCUMENTS

| | | | | |
|---|---|---|---|---|
| KR | 10-2012-0049085 A | 5/2012 | | |
| KR | 20-2013-0000537 U | 1/2013 | | |
| KR | 20140053681 A | 5/2014 | | |
| KR | 20160140176 A | 12/2016 | | |
| KR | 101741067 B1 * | 5/2017 | ............ | A45D 44/22 |

* cited by examiner

FACIAL MASK FOR SKIN CARE

CROSS REFERENCE TO RELATED APPLICATIONS

This application is a 35 U.S.C. 371 National Phase Entry Application from PCT/KR2020/007671, filed Jun. 12, 2020, designating the United States, which claims the benefit of Korean Patent Application No. 10-2019-0070372 filed on Jun. 14, 2019, the disclosures of which are incorporated herein in their entirety by reference.

TECHNICAL FIELD

The present invention relates to a facial mask for skin care.

BACKGROUND ART

As interest in cosmetic treatments has increased, a variety of cosmetic apparatuses and the like have been developed. Due to such interest in cosmetic treatments, attention has focused on skin, particularly, on facial skin and a variety of cosmetics or cosmetic apparatuses for enhancing conditions of facial skin have been developed.

Among these cosmetic apparatuses, a cosmetic apparatus formed in a mask type to be worn on a head part and including light emitting devices (LEDs) on a side facing the skin to emit far-infrared rays, near-infrared rays, or the like or to stimulate the skin with ultrasonic waves or low frequencies so as to improve elasticity of the skin, to promote blood circulation, or to promote absorption of cosmetics has been developed.

However, since a conventional mask-shaped cosmetic apparatus is formed of a hard material without flexibility and is difficult to press against the face, a user is caused to be uncomfortable when being active while wearing the apparatus on a head part and thus user complaints have been lodged.

Also, when vibrations such as ultrasonic waves, low frequencies, or the like are applied to the skin, a plurality of vibrators generating vibrations are mounted and only some of the plurality of vibrators are operated or the plurality of vibrators generate vibrations at different frequencies according to an operational mode. Here, since the vibrators are coupled to one circuit board and mask body so that vibrations generated by any one of the plurality of vibrators are transferred to an entirety of a mask and applied to an entirety of the face, there is a difficulty in locally applying vibrations to any one part or applying different frequencies.

DISCLOSURE

Technical Problem

The present invention is directed to providing a skin care mask pressed against the face to allow a user to act comfortably while wearing the skin care mask and configured to locally apply vibrations to a desired region of the face.

Technical Solution

One aspect of the present invention provides a skin care mask including a mask member placed on a facial region of a human body, one or more vibrators installed in the mask member to transfer vibrations to the skin, an operating part configured to transfer the vibrations of the vibrators toward the skin and to prevent the vibrations from being transferred to the mask member, and a control part configured to separately control a plurality of such vibrators.

The mask member may include an outer coating facing an outside of the face and configured to form an exterior and an inner coating provided on an inside of the outer coating which faces the skin.

The outer coating and the inner coating may be formed of a flexible material.

The outer coating and the inner coating may be formed of thermoplastic polyurethane (TPU) or thermoplastic elastomers (TPEs).

One or more of the vibrators may be provided on a side of the inner coating which comes into contact with the skin.

The operating part may include a vibration transfer member having one surface coming into contact with the vibrator and the other surface coming into contact with the skin so as to transfer the vibrations of the vibrators to the skin and a vibration absorption member disposed between the vibrator and the inner coating to absorb the vibrations of the vibrator not to be transferred to the inner coating.

The vibration transfer member may be formed to have an area larger than the vibrator.

The vibration absorption member may be formed of a flexible material having hardness lower than the inner coating and may be formed on an outer periphery of the vibration transfer member.

The inner coating and the vibration absorption member may be integrally formed through insert-injection molding.

The vibration transfer member, the vibration absorption member, and the inner coating may be formed to have the same thickness and be coplanar with one another.

The vibration absorption member may have a thickness formed to be smaller than thicknesses of the vibration transfer member and the inner coating.

At least part of an outer edge of the vibration absorption member may be embedded and accommodated in the inner coating, and at least part of an inner edge of the vibration absorption member may be embedded and accommodated in the vibration transfer member.

The skin care mask may further include a functional patch unit disposed on another part different from a skin part vibrated by the vibrator.

The functional patch unit may be replaceably provided and may be at least one of a vibration patch configured to apply vibrations, a thermal patch, and a light emitting device (LED) patch.

A patch mount portion recessed to allow the functional patch portion to be mounted thereon may be formed in the inner coating.

The functional patch unit may be disposed on the patch mount portion.

The control part may include a processor configured to separately control the vibrator and a circuit board on which the processor is mounted and may be provided between the outer coating and the inner coating.

The circuit board may be a flexible printed circuit board (FPCB).

The vibrator may be mounted on the circuit board.

Power supplied to the control part and the vibrators may be supplied by a battery or an external power source.

Another aspect of the present invention provides a skin care mask including a mask member placed on a facial region of a human body and comprising an outer coating formed of a flexible material having flexibility, configured to form an exterior, and in which a region corresponding to an eyeball of the face is opened so that a view hole is formed, an inner coating provided inside the outer coating facing the skin, and straps formed on both sides of the outer coating to be fixed to a head part of the human body, a plurality of vibrators in which one or more vibrators are provided on a side of the inner coating which comes into contact with the skin and transfer vibrations to the skin, a control part provided between the outer coating and inner coating and comprising a processor configured to separately control the vibrator and an FPCB on which the processor and the vibrators are mounted, and an operating part comprising a vibration transfer member having one surface coming into contact with the vibrators and the other surface coming into contact with the skin to transfer the vibrations of the vibrators to the skin and a vibration absorption member integrally formed with the inner coating and the vibration transfer member through insert-injection molding and formed of a flexible material having hardness lower than the inner coating to absorb and prevent the vibrations of the vibrators from being transferred to the inner coating so as to transfer the vibrations of the vibrators toward the skin and to cut off the vibrations transferred to the mask member.

Advantageous Effects

According to the present invention, since a vibrator is vibration-isolated from a periphery by a vibration isolator, vibrations of the vibrator are cut off so as not to be transferred to another part so that there is an effect of locally transferring vibrations.

Also, since the vibrations are locally transferred, there is an effect of more definitely dividing a variety of operational modes in which only some of a plurality of such vibrators operate or the plurality of vibrators operate at different frequencies.

Also, since vibrations are transferred only toward the skin and not transferred to a periphery, there is an effect of further increasing vibration energy transferred to the skin.

Also, since flexibility is formed overall, it is possible to press a mask against the face so that there is an effect of increasing activity while wearing.

MODES OF THE INVENTION

Figure 1:
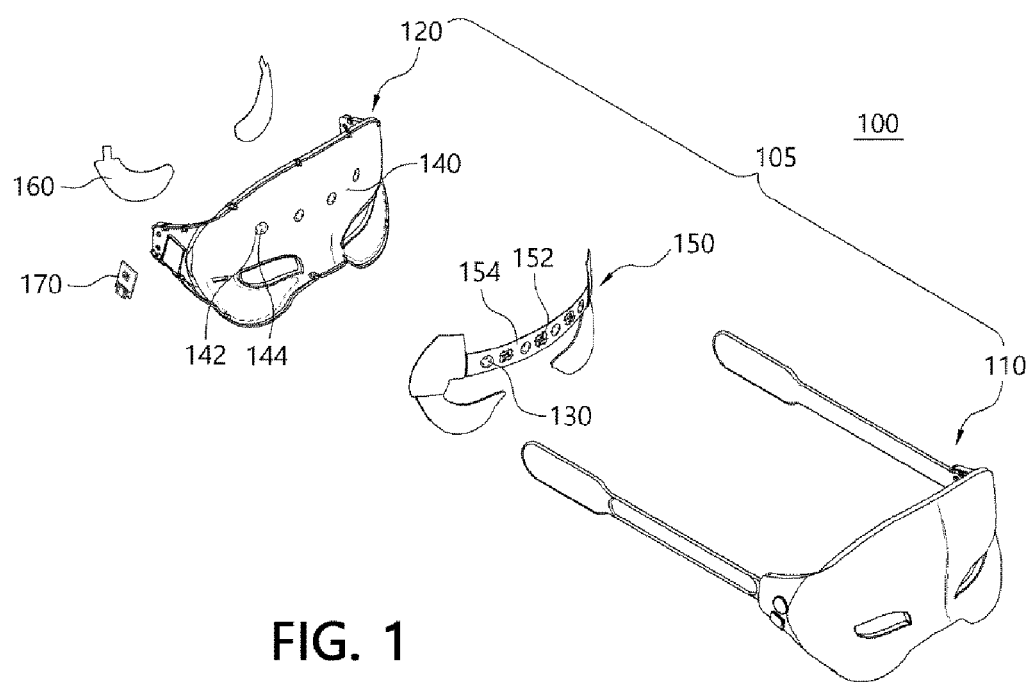
FIG. 1 is an exploded perspective view illustrating a mask for skin care according to one embodiment of the present invention.

Hereinafter, embodiments of the present invention will be described in detail to be implemented by one of ordinary skill in the art with reference to the drawings. The present invention may be implemented in a variety of shapes and will not be limited to the embodiments described herein. To clearly describe the present invention, irrelevant parts will be omitted from the drawings. Throughout the specification, like or similar components will be referred to as like reference numerals.

Figure 2:
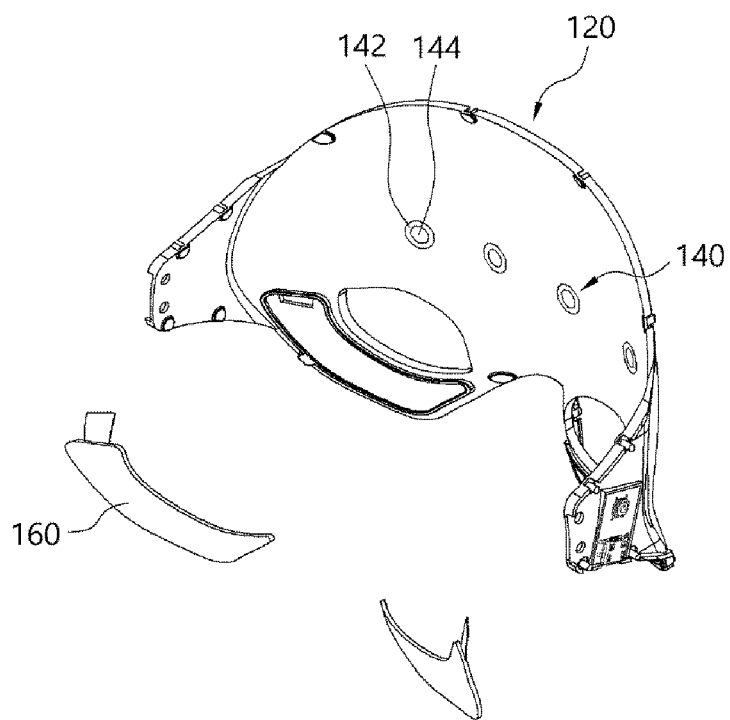
FIG. 2 is a perspective view illustrating a rear surface of an inner coating of FIG. 1.

The skin care mask 100 according to one embodiment of the present invention may include, as shown in FIGS. 1 and 2, a mask member 105, a vibrator 130, an operating part 140, and a control part 150.

The mask member 105 is put on a facial region of a human body and may include an outer coating 110 and an inner coating 120.

The outer coating 110 and the inner coating 120 have a shape corresponding to a facial shape overall and may be formed of an elastic and flexible material so as to be pressed against the user's face while being worn thereon.

The outer coating 110 may form an exterior and be formed to have a shape like a mask corresponding to the facial shape and including a view hole 114 opened to provide a user's view in a region corresponding to eyes and a strap 112 or the like to be worn on a head region.

In the embodiment, it will be described as an example that the outer coating 110 is formed to cover a forehead, a part around eyes, cheekbones, and at least a part of cheeks of the face while a nose, a mouth, a chin, and the like are open. However, the present invention is not limited thereto and may be formed to cover an overall face according to an embodiment.

The inner coating 120 may be formed of a flexible material having flexibility like the outer coating 110 and may be formed to be coupled to a rear surface that is a surface of the outer coating 110 facing the skin.

Here, the inner coating 120 may be implemented to form a face covering region similar to the outer coating 110. The face cover region may be a region of the face of the head part covered by the outer coating 110 or the inner coating 120. However, the present invention is not limited thereto, and the inner coating 120 may be formed to have the face cover region that is larger or smaller than the outer coating 110.

Meanwhile, the outer coating 110 and the inner coating 120 may employ a material having elasticity and flexibility such as thermoplastic elastomers (TPEs), thermoplastic polyurethane (TPU), or the like but are not limited thereto and may employ any material capable of maintaining hardness strong enough to maintain adequate elasticity, flexibility, and its shape.

The vibrator 130 is a component installed in the mask member 105 to transfer vibrations to the skin so as to enhance skin elasticity, promote blood circulation, and promote absorption of cosmetics and the like, and one or more such vibrators 130 may be provided at certain intervals on a side of the inner coating 120 in contact with the skin.

In the embodiment, although the vibrator 130 will be described, as an example, as being disposed at a position of the inner coating 120 corresponding to the forehead of the face, an installation position thereof may change and the installation position of the vibrator 130 is not limited in the present invention.

Also, the vibrator 130 may include a vibration motor or the like. In addition, any of an ultrasonic oscillator, a low-frequency oscillator, or the like which is capable of providing stimuli, such as vibrations, ultrasonic waves, low frequencies, or the like, to the skin may be applied thereto.

Figure 3:
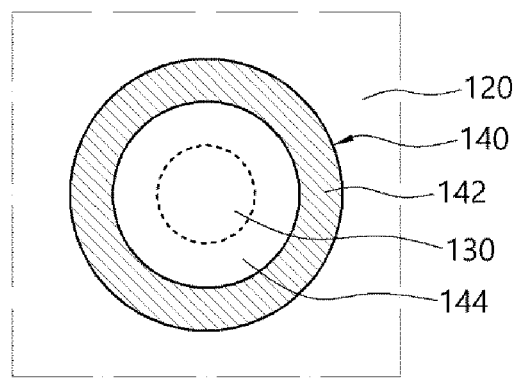
FIG. 3 is a plane view illustrating a state in which a vibrator is coupled to an operating part.

The operating part 140 is a component configured to transfer vibrations, ultrasonic waves, low frequencies, or the like of the vibrator 130 toward the skin and configured to prevent vibrations transferred to the mask member 105 and may include a vibration absorption member 142 and a vibration transfer member 144 as shown in FIG. 3.

That is, the operating part 140 is integrally formed with the inner coating 120. The vibration transfer member 144 of the operating part 140 has one surface coming into contact with the vibrator 130 and the other surface coming into contact with the skin so as to transfer vibrations of the vibrator 130 to the skin.

Also, the vibration absorption member 142 may be disposed between the vibration transfer member 144 and the inner coating and absorb the vibrations of the vibrator 130 not to be transferred to the inner coating 120 so as to locally transfer the vibrations of the vibrator 130 only to the skin and to prevent the vibrations from being transferred to the inner coating 120.

The vibration absorption member 142 may be formed of a flexible material having hardness lower than the inner coating 120 and formed to surround a periphery of the vibrator 130 so as to absorb and prevent the vibrations of the vibrator 130 from being transferred to the inner coating 120.

A material of the vibration absorption member 142 may be, for example, TPE, TPU, silicone, or the like but is not limited thereto, and may be any materials having hardness lower than the inner coating 120 or effectively absorbing and preventing vibrations and harmless to a human body.

Also, the vibration transfer member 144 may be formed to have the same material and hardness as the inner coating 120.

Figure 4:
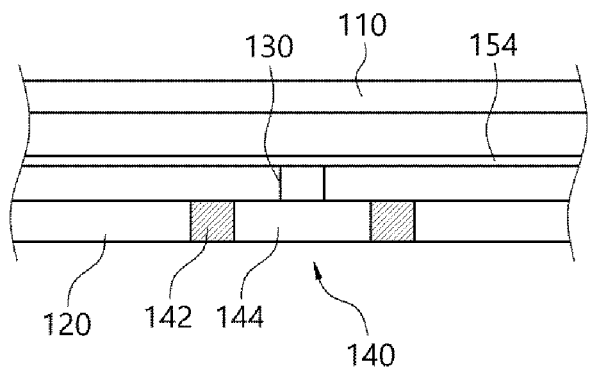
FIG. 4 is a cross-sectional view illustrating one example of a cross section of a coupled part where the vibrator is coupled to the operating part.

The vibration absorption member 142 may be formed, as shown in FIGS. 3 and 4, to surround a part around the vibrator 130 so as to vibration-isolate the inner coating 120 from the vibrator 130.

Also, the vibration absorption member 142 may be integrally formed with the inner coating 120 and the vibration transfer member 144 through insert-injection molding.

A shape of the vibration absorption member 142 will be described in detail. As shown in FIGS. 3 and 4, the vibration transfer member 144 may have an area larger than or equal to the vibrator. The vibration absorption member 142 may be formed to surround an outer periphery of the vibration transfer member 144 while an inner circumferential surface may be insert-injection molded with the vibration transfer member 144 and an outer circumferential surface may be insert-injection molded with the inner coating 120 to be integrally formed.

Also, the vibration transfer member 144 may be formed to have a disc shape, and the vibration absorption member 142 may be formed to have a ring shape. In addition, the vibration transfer member 144 and the vibration absorption member 142 may be formed to have a variety of shapes.

In the embodiment, a surface of the vibration transfer member 144 coming into contact with the skin is described, as an example, as being formed to be even but is not limited thereto and may include a pointed or rounded protrusion on a surface facing the skin.

Also, a surface of the vibration transfer member 144 coming into contact with the vibrator 130 is described, as an example, as being formed to be even but is not limited thereto and may include a groove or edge which forms a space in which the vibrator 130 is partially accommodated so as to effectively transfer the vibrations of the vibrator 130.

Accordingly, the vibrations of the vibrator 130 may be transferred to the skin through the vibrator 130 or the vibration transfer member 144 and vibrations transferred to the inner coating 120 may be cut off by the vibration absorption member 142 so that vibrations may be locally applied only to a skin part coming into contact with the vibrator 130 or the vibration transfer member 144.

Also, as shown in FIG. 4, the vibration absorption member 142 may be formed to have the same thickness as the inner coating 120 and the vibration transfer member 144, and all of the inner coating 120, the vibration absorption member 142, and the vibration transfer member 144 may be formed as the same plane.

Figure 5:
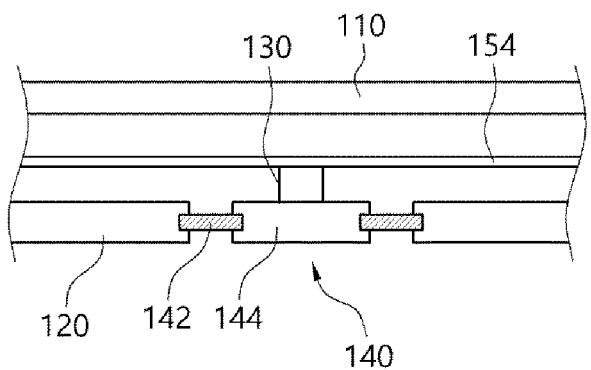
FIG. 5 is a cross-sectional view illustrating another example of a cross section of a coupled part where the vibrator is coupled to the operating part.

Also, as shown in FIG. 5, the thickness of the vibration absorption member 142 may be formed to be smaller than the inner coating 120 and the vibration transfer member 144, and at least parts of an inner edge and an outer edge may be embedded in the vibration transfer member 144 and the inner coating 120 through insert-injection molding.

In addition, the vibration transfer member 144 may be formed to protrude further toward the skin side than the inner coating 120 and the vibration absorption member 142.

Meanwhile, the control part 150 is a component configured to separately control the plurality of vibrators 130 and may include a circuit board 154 and a processor 152 which are provided between the outer coating 110 and the inner coating 120.

The circuit board 154 is provided between the outer coating 110 and the inner coating 120, and the processor 152 is mounted on the circuit board 154 and may separately control each of the vibrators 130. However, in addition to the processor 152, a variety of necessary components and devices may be mounted on the circuit board 154.

Meanwhile, since the outer coating 110 and the inner coating 120 have flexibility, the circuit board 154 may also be formed of a flexible printed circuit board (FPCB) or the like which has flexibility. However, according to the present invention, the circuit board 154 is not limited to the FPCB having flexibility and, if necessary, may be formed of a general hard printed circuit board (PCB) or may be formed to have a shape divided into a plurality of hard PCBs to have flexibility with spaces therebetween being connected using wires such as a film or the like having flexibility.

Also, the vibrator 130 may be mounted on the circuit board 154.

In this case, the circuit board 154 may be provided at a position corresponding to a position of the face to which the vibrator 130 applies vibrations. That is, when the vibrator 130 is provided to apply vibrations to the forehead of the face, the circuit board 154 is also provided at a position corresponding to the forehead between the outer coating 110 and the inner coating 120.

Accordingly, the vibrations of the vibrator 130 are locally transferred only to the skin in contact with the vibration transfer member 144 and do not spread toward another part. However, although the vibrator 130 is directly mounted on the circuit board 154, since a flexible circuit board 154 is applied as the circuit board 154 on which the vibrator 130 is mounted to also have flexibility, the flexible circuit board 154 having flexibility may perform a function of reducing vibrations so as to cut off and reduce vibrations transferred to other parts such as the outer coating 110, the inner coating 120, and the like which come into contact with the control part 150.

Also, since the vibrations are locally transferred, there is an effect of more definitely dividing a variety of operational modes in which only some of the plurality of vibrators 130 operate or the plurality of vibrators 130 operate at different frequencies.

Meanwhile, the skin care mask 100 according to the embodiment may further include a functional patch unit 160.

As shown in FIGS. 1 and 2, the functional patch unit 160 is configured to provide skin treatment to another part different from a part vibrated by the vibrator 130 and may be detachably provided on the inner coating 120 and the control part 150.

As described above, since the vibrator 130 has been described as corresponding to the forehead as an example, in the embodiment, the functional patch unit 160 may be provided to give treatment to a part around eyes, a part of cheeks, cheekbones, or a temple-coordinate part.

To this end, one or more functional patch units 160 may be provided on a rear surface of the inner coating 120 which faces the skin.

Also, a patch mount portion 124 on which the functional patch unit 160 is mounted may be formed for each part of the rear surface of the inner coating 120. The patch mount portion 124 may be formed as a groove or have an edge with a shape corresponding to a shape of the functional patch unit 160 mounted thereon so as to allow a user to simply mount the functional patch unit 160 on a regular position.

Also, the functional patch unit 160 is detachably provided and may perform each of functions of providing vibrations, warmth, or light of a light emitting device (LED) or the like so that the functional patch unit 160 performing a desired function as necessary is selected and mounted.

Also, the functional patch unit 160 may include a patch connection portion 156 detachably coupled to the circuit board 154 of the control part 150, a component mounted on the circuit board 154, or the like, and the control part 150 may be provided to control the functional patch unit 160.

The patch mount portion 124 may include a slit 126 or hole through which a wire or the like may pass so that the patch connection portion 156 of the control part 150 and a replaceable patch are connected.

Accordingly, the functional patch unit 160 performing a desired function may be mounted on a part desired by the user to be used.

However, when the functional patch unit 160 includes a vibration function, like the above vibrator, a periphery of a component generating vibrations may be vibration-isolated so as not to transfer the vibrations to another part.

However, the functional patch unit 160 may not necessarily be provided to be detachable and may be installed to be fixed to the inner coating 120 not to be replaceable as necessary.

Also, a controller 170 configured to receive and transfer manipulation of the user to the control part 150 may be provided. The controller 170 may be provided between the outer coating 110 and the inner coating 120 of a side surface of the mask member 105 and may include a button or the like for receiving input of the user which is exposed through the outer coating 110 to receive manipulation through an operation of pushing the button.

Also, a battery (not shown) configured to supply power to the control part 150, the vibrator, and the functional patch unit 160 may be provided with the controller 170.

The battery may be a rechargeable battery that can be reused or a replaceable battery.

In addition, the battery may be provided with the control part 150 or may be a flexible battery corresponding to distortion of the outer coating 110 or the inner coating 120.

Otherwise, external power may be input instead of the battery.

Otherwise, the controller 170 may be a remote controller 170 (not shown) separately provided and not provided between the outer coating 110 and the inner coating 120.

The remote controller 170 is connected to the control part 150 wirelessly or through wires and may include a button portion configured to receive input of the user and a display configured to display a variety of pieces of information such as an input item, progress, and the like. Also, when the remote controller 170 is connected through wires, the battery configured to supply power to the control part 150 and the vibrator 130 may be built in the remote controller 170.

Alternatively, an additional controller is not provided and an application installed in a smart phone belonging to the user may receive the manipulation. In this case, the control part 150 may include a wireless connection function such as Bluetooth or the like to be connectable to the smart phone. In addition, a variety of devices and a variety of modifications are available.

Although one embodiment of the present invention has been described above, the concept of the present invention is not limited to the embodiment disclosed herein and it should be understood that one of ordinary skill in the art who understands the concept of the present invention may easily provide other embodiments through addition, changes, deletion, and the like of components without departing from the scope of the same concept which will be included in the scope of the concept of the present invention.

The invention claimed is:

1. A skin care mask comprising:
a mask member configured to be placed on a facial region of a human body;
one or more vibrators installed within the mask member and configured to transfer vibrations to skin of the human body;
a vibration absorption member;
a vibration transfer member including a first surface contacting the one or more vibrators, a second surface configured to contact the skin, and an outer periphery facing an inner coating, wherein the vibration transfer member is configured to transfer the vibrations of the one or more vibrators to the skin; and
a processor configured to separately control the one or more vibrators,
wherein the mask member comprises:
an outer coating configured to form an exterior and face away from the facial region when the mask member is placed on the facial region; and
the inner coating disposed on an inside of the outer coating and configured to face the skin,
wherein the vibration absorption member is disposed between the vibration transfer member and the inner coating to 1) surround the outer periphery of the vibration transfer member facing the inner coating and 2) absorb the vibrations of the one or more vibrators to prevent the vibrations from being transferred to the inner coating.

2. The skin care mask of claim 1, wherein the outer coating and the inner coating are formed of a flexible material.

3. The skin care mask of claim 2, wherein the outer coating and the inner coating are formed of thermoplastic polyurethane (TPU) or thermoplastic elastomers (TPEs).

4. The skin care mask of claim 1, wherein the vibration transfer member has an area larger than the one or more vibrators.

5. The skin care mask of claim 1, wherein the vibration absorption member is formed of a flexible material having a hardness lower than the inner coating.

6. The skin care mask of claim 1, wherein the inner coating and the vibration absorption member are integrally disposed through insert-injection molding.

7. The skin care mask of claim 5, wherein the vibration transfer member, the vibration absorption member, and the inner coating have a thickness and be coplanar with one another.

8. The skin care mask of claim 5, wherein the vibration absorption member has a thickness smaller than thicknesses of the vibration transfer member and the inner coating.

9. The skin care mask of claim 8, wherein a part of an outer edge of the vibration absorption member is embedded and accommodated in the inner coating, and
wherein a part of an inner edge of the vibration absorption member is embedded and accommodated in the vibration transfer member.

10. The skin care mask of claim 1, further comprising a functional patch unit disposed on a first skin part different from a second skin part vibrated by the one or more vibrators.

11. The skin care mask of claim 10, wherein the functional patch unit is configured to be replaced.

12. The skin care mask of claim 10, wherein the inner coating comprises a patch mount portion recessed into the inner coating to allow the functional patch unit to be mounted thereon, and
wherein the functional patch unit is disposed on the patch mount portion.

13. The skin care mask of claim 1, further comprising:
a circuit board on which the processor is mounted,
wherein the processor is provided between the outer coating and the inner coating.

14. The skin care mask of claim 13, wherein the circuit board is a flexible printed circuit board (FPCB).

15. The skin care mask of claim 13, wherein the one or more vibrators are mounted on the circuit board.

16. A skin care mask comprising:
a mask member configured to be placed on a facial region of a human body, wherein the mask member comprises:
an outer coating formed of a flexible material having flexibility and configured to form an exterior, wherein the outer coating includes a view hole corresponding to an eye of the facial region,
an inner coating disposed on an inside of the outer coating and configured to face skin of the facial region, and
straps formed on a first side and a second side of the outer coating and configured to be fixed to a head part of the human body;
a plurality of vibrators provided on a side of the inner coating configured to contact the skin, wherein the plurality of vibrators are configured to transfer vibrations to the skin;
a processor provided between the outer coating and the inner coating and configured to separately control the plurality of vibrators;
a vibration transfer member including a first surface contacting the plurality of vibrators, a second surface configured to contact the skin, and an outer periphery facing the inner coating, wherein the vibration transfer member is configured to transfer the vibrations of the plurality of vibrators to the skin; and
a vibration absorption member integrally formed with the inner coating and the vibration transfer member through insert-injection molding, wherein the vibration absorption member is formed of a flexible material having a hardness lower than the inner coating to absorb and prevent the vibrations of the plurality of vibrators from being transferred to the inner coating, and
wherein the vibration absorption member is disposed between the vibration transfer member and the inner coating to surround the outer periphery of the vibration transfer member facing the inner coating.

* * * * *